(12) United States Patent
Muller et al.

(10) Patent No.: US 7,666,629 B2
(45) Date of Patent: Feb. 23, 2010

(54) METHOD FOR PRODUCING RECOMBINANT TRYPSIN

(75) Inventors: Rainer Muller, Penzberg (DE); Stephan Glaser, Seeshaupt (DE); Frank Geipel, Penzberg (DE); Johann-Peter Thalhofer, Weilheim (DE); Bernhard Rexer, Weilhem (DE); Claus Schneider, Eppelheim (DE); Michael Ratka, Mannheim (DE); Stephanie Ronning, Penzberg (DE); Hellmut Eckstein, Weilheim (DE); Claudia Giessel, Greiling (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/853,483

(22) Filed: Sep. 11, 2007

(65) Prior Publication Data

US 2008/0064084 A1 Mar. 13, 2008

Related U.S. Application Data

(62) Division of application No. 10/470,508, filed as application No. PCT/EP02/01072 on Feb. 1, 2002, now Pat. No. 7,276,605.

(30) Foreign Application Priority Data

Feb. 1, 2001 (EP) .................................. 01102342

(51) Int. Cl.
*C12N 15/62* (2006.01)
*C12N 9/76* (2006.01)
*C12N 15/79* (2006.01)
*C12N 15/81* (2006.01)

(52) U.S. Cl. .................... 435/69.7; 435/226; 435/252.3; 435/254.2; 435/254.23; 435/320.1; 536/23.4

(58) Field of Classification Search ........................ None
See application file for complete search history.

(56) References Cited

U.S. PATENT DOCUMENTS

| 4,851,341 | A | * | 7/1989 | Hopp et al. ................. 435/69.7 |
| 5,011,912 | A | * | 4/1991 | Hopp et al. ............... 530/387.9 |
| 5,298,599 | A | * | 3/1994 | Rezaie et al. ................ 530/350 |
| 5,472,692 | A | * | 12/1995 | Liu et al. .................... 424/94.63 |
| 5,760,189 | A | * | 6/1998 | Vicik et al. .................. 530/412 |
| 5,945,328 | A | | 8/1999 | Woldike et al. |
| 6,087,558 | A | * | 7/2000 | Howard et al. ............... 800/278 |
| 6,143,524 | A | * | 11/2000 | McCoy et al. ............... 435/69.7 |
| 6,159,722 | A | * | 12/2000 | Bode et al. .................. 435/219 |
| 6,171,842 | B1 | * | 1/2001 | Bode et al. .................. 435/219 |
| 6,420,157 | B1 | | 7/2002 | Darrow et al. |
| 6,444,644 | B1 | * | 9/2002 | Bruckdorfer et al. .......... 514/12 |
| 6,458,564 | B1 | | 10/2002 | Darrow et al. |
| 6,485,957 | B1 | | 11/2002 | Darrow et al. |
| 6,486,303 | B1 | * | 11/2002 | Moyle ....................... 530/387.3 |
| 6,632,638 | B1 | * | 10/2003 | Snavely et al. .............. 435/69.1 |
| 6,660,492 | B1 | * | 12/2003 | Bode et al. ..................... 435/23 |
| 6,881,411 | B2 | * | 4/2005 | Stewart et al. ............ 424/184.1 |
| 6,906,176 | B2 | * | 6/2005 | Ley et al. ..................... 530/350 |
| 7,029,909 | B1 | * | 4/2006 | Uemura et al. ............. 435/320.1 |
| 7,030,223 | B2 | * | 4/2006 | Turner et al. ................. 530/351 |
| 7,063,961 | B2 | * | 6/2006 | Ballinger et al. ........... 435/69.1 |
| 7,172,892 | B2 | * | 2/2007 | Madison et al. .............. 435/226 |
| 7,247,453 | B1 | * | 7/2007 | Rezaie et al. ............... 435/69.6 |
| 7,276,605 | B2 | * | 10/2007 | Muller et al. ............... 435/69.1 |
| 7,351,549 | B2 | * | 4/2008 | Mattanovich et al. ....... 435/69.1 |
| 2002/0102709 | A1 | * | 8/2002 | Ishikawa et al. ............. 435/226 |
| 2002/0115833 | A1 | * | 8/2002 | Burg et al. ................... 530/395 |
| 2002/0155547 | A1 | * | 10/2002 | Whitty et al. ............. 435/69.51 |
| 2002/0177545 | A1 | * | 11/2002 | Donovan ........................ 514/2 |
| 2003/0017531 | A1 | * | 1/2003 | Werner et al. .............. 435/69.1 |
| 2003/0157634 | A1 | | 8/2003 | Mattanovich et al. |
| 2003/0207402 | A1 | | 11/2003 | Kopetzki et al. |

FOREIGN PATENT DOCUMENTS

| DE | 249282 | 9/1987 |
| EP | 0 597 681 | 5/1994 |
| EP | 0 699 687 | 3/1996 |
| EP | 1012307 | 6/2000 |
| JP | 11-507207 | 6/1999 |
| WO | WO 97/00316 | 1/1997 |
| WO | WO 99/10503 | 3/1999 |
| WO | WO 00/17332 | 3/2000 |
| WO | WO 01/19970 | 3/2001 |
| WO | WO 01/55429 | 8/2001 |

OTHER PUBLICATIONS

Koshikawa, N., et al., 1994, "Identification of one- and two-chain forms of trypsinogen 1 produced by a human gastric adenocarcinoma cell line", Biochemical Journal, Vol. 303, pp. 187-190.*
Vestling, M.M., et al., "Recognition of Trypsin Autolysis Products by High-Performance Liquid Chromatography and Mass Spectrometry," Anal. Chem. 1990, 2, pp. 2391-2394.
Walker, J.E. et al., "Purification and Characterisation of Different Active forms of Pork Trypsin," Ear. J. Biochem., 32, pp. 486-491 (1973).
Rice, R.H., et al., "Stabilization of Bovine Trypsin by Reductive Methylation," Biochemica et Biophysica Acta, 492 (1977), 316-321.
Hedstrom L. et al., "Converting Trypsin to Chymotrypsin: The Role of Surface Lops," Science, vol. 255, Mar. 6, 1992, pp. 1249-1253.
Brodrick, J.W. et al., "Human Cationic Trypsinogen-Purification, Characterization, and Characteristics of Autoactivation," The Journal of Biological Chemistry, vol. 263, No. 8, Apr. 26, 1978, pp. 2732-2736.
Keil, B., "Trypsin," The Enzymes vol. II, $3^{rd}$ Edition, Acad. Press, N.Y., 1971, pp. 249-275.

(Continued)

Primary Examiner—Anand U Desai
Assistant Examiner—William W Moore
(74) Attorney, Agent, or Firm—Barnes & Thornburg LLP

(57) ABSTRACT

The present invention concerns a method for producing recombinant trypsin from porcine pancreas in *Pichia pastoris* which is soluble and secreted into the culture medium, whereby expression at pH 3.0-4.0 substantially prevents activation of trypsinogen to β-trypsin and autolysis of β-trypsin by α-trypsin into ε-trypsin and from there into inactive peptides.

4 Claims, 3 Drawing Sheets

OTHER PUBLICATIONS

Figure 1:
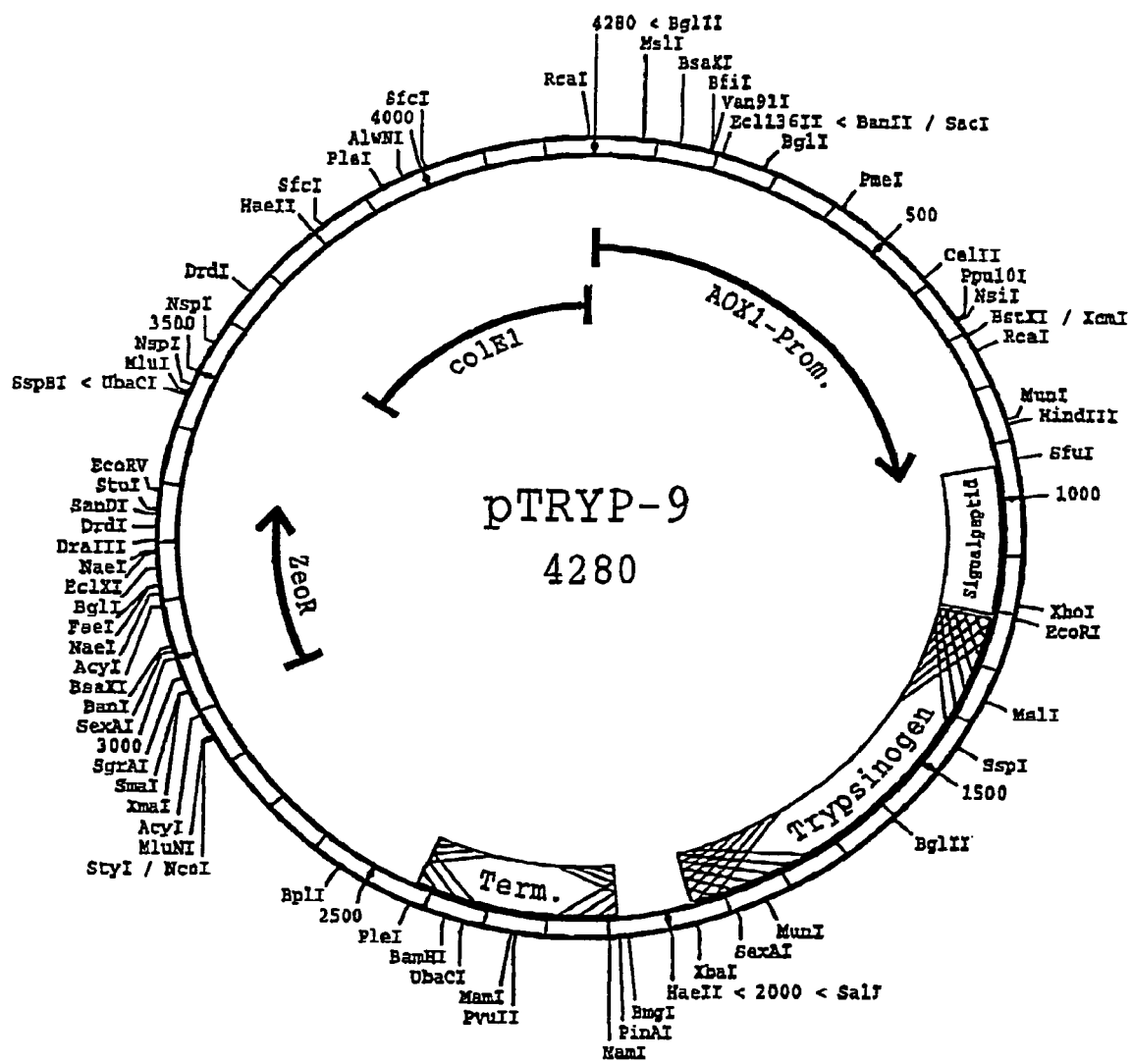

XP-00223000, publication date: Jul. 21, 1986, p. 1-3.

XP-002171427, publication date: Jul. 21, 1986, p. 1-4.

Boyer, Paul D., "The Enzymes," USA, Academic Press, 1971, 249-275.

Cregg et al., Biotechnology, 1993, 11(8), 905-910.

Emi, Mitsuru et al., Cloning, Characterization and Nucleotide Sequences of Two cDNAs Encoding Human Pancreatic Trypsinogens, Gene 41 (1986), 305-310.

Vasquez, J. et al., "An Expression System for Trypsin," Cell. Biochemistry 39:265-276 (1989).

Sharp, P. et al., "The Codon Adaptation Index—A Measure of Directional Synonymous Codon Usage Bias, And Its Potential Applications," Nucleic Acids Research vol. 15, No. 3, 1987, 1281-1295.

Liener, I.E., "Chromatographic Studies on Trypsin, Trypsinogen And The Activation Process," Biochem. Biophys. 88 (1960), 216-221.

Graf, L. et al., "Selective Alteration of Substrate Specificity by Replacement of Aspartic Acid-189 with Lysine in the Binding Pocket of Trypsin," Biochemistry, vol. 26, (1987), 2616-2623.

* cited by examiner

Figur 2
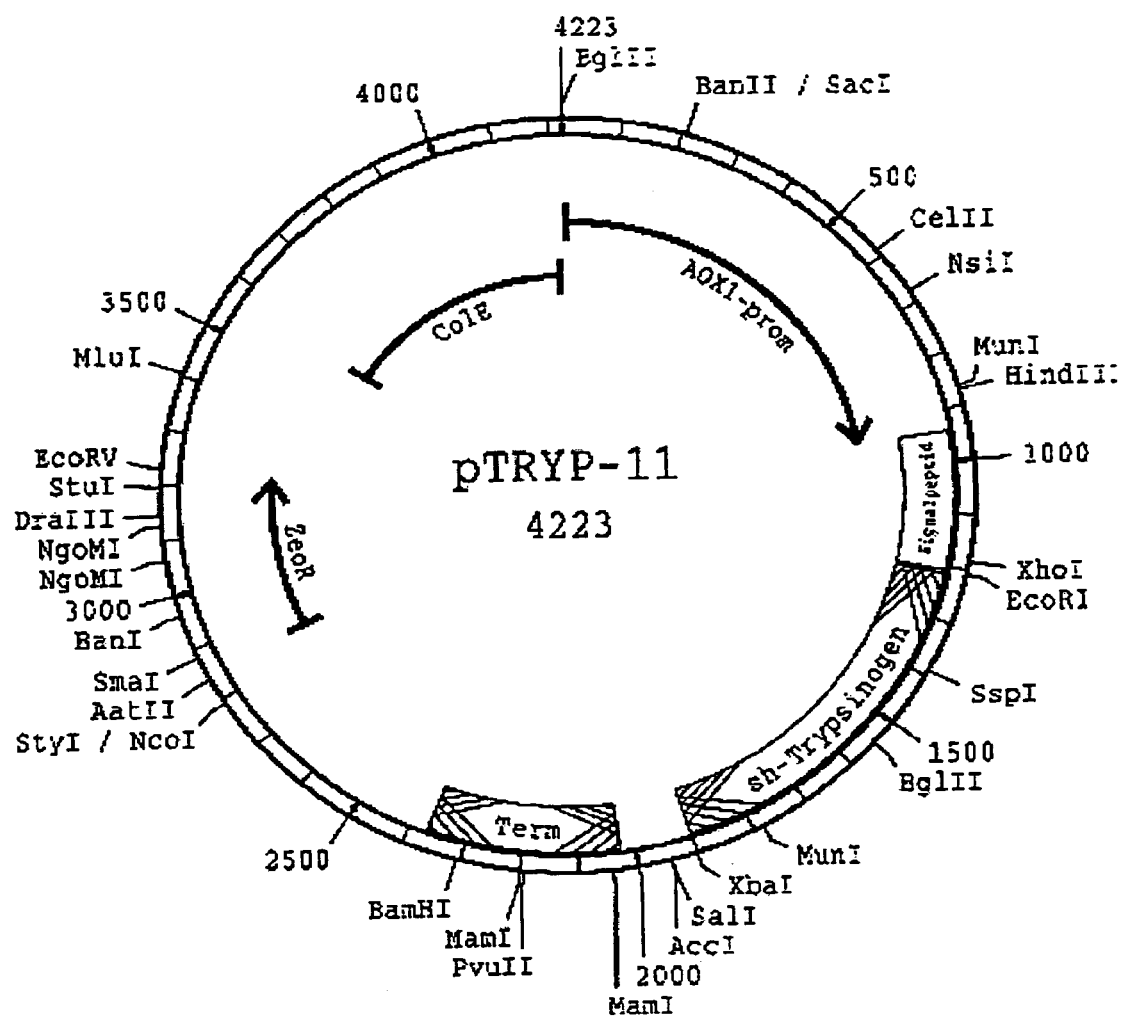

Figur 3
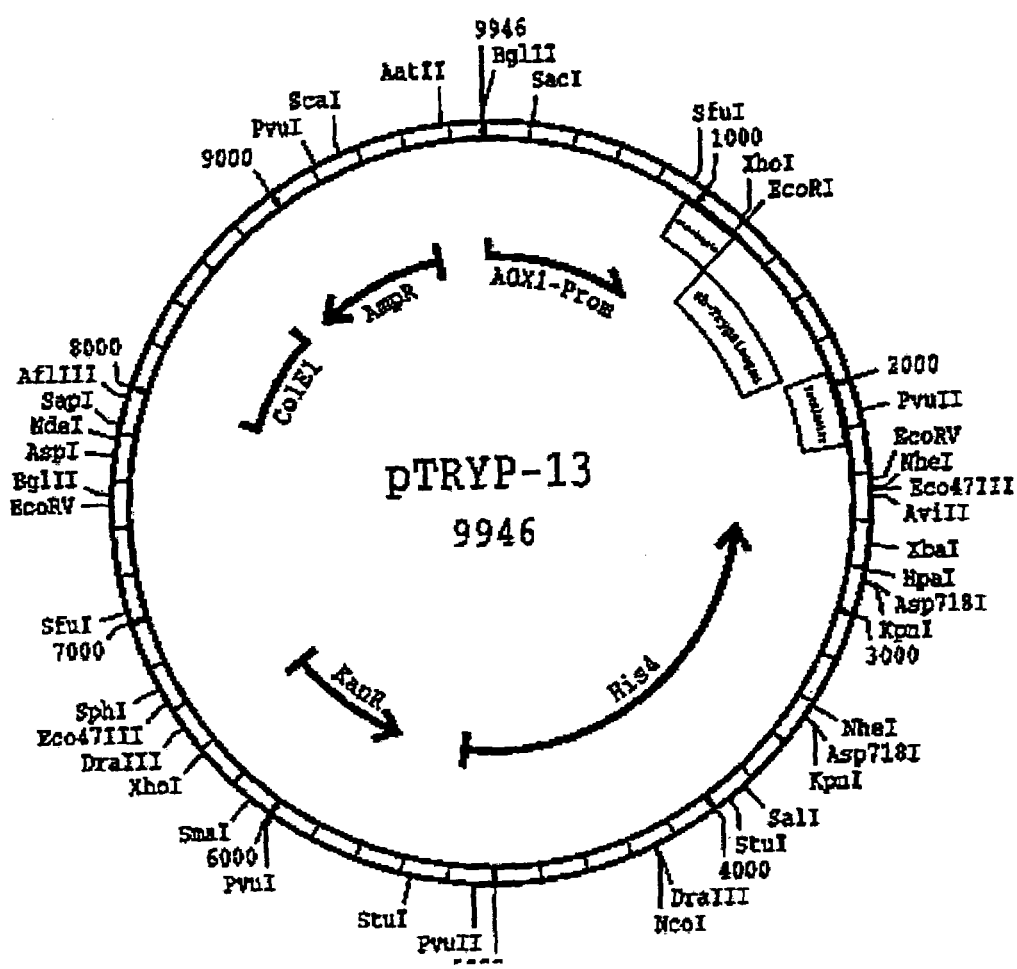

METHOD FOR PRODUCING RECOMBINANT TRYPSIN

CROSS-REFERENCE TO RELATED APPLICATION

This application is a divisional of U.S. patent application Ser. No. 10/470,508, filed Apr. 12, 2004, now U.S. Pat. No. 7,276,605, which is a U.S. national counterpart application of international application serial No. PCT/EP02/01072, filed Feb. 1, 2002, which claims the benefit of European application No. 01102342.1, filed Feb. 1, 2001.

DESCRIPTION

The invention concerns a method for the recombinant production of trypsin. For this purpose a trypsinogen with a shortened propeptide sequence is preferably expressed in a recombinant host cell and secreted into the culture medium in an uncleaved form. Subsequently the propeptide sequence is cleaved in a controlled manner to form active trypsin.

Trypsin is a serine protease which catalyses a hydrolytic cleavage of peptides at the carboxyl group of the basic amino acids arginine and lysine (Keil B., 1971). Trypsin from bovine pancreas was one of the first proteolytic enzymes that could be used in a pure form and in adequate quantities for exact chemical and enzymatic studies (Northrop et al., 1948). It was subsequently also possible to isolate proteases that can be allocated to the trypsin family from other higher vertebrates (pig—Charles et al. 1963/sheep—Bricteux-Gregoire et al. (1966); Travis (1968)/turkey —Ryan (1965)/humans—Travis et al. (1969) and others). At this time the first enzymes belonging to the trypsin family were also isolated from two species of streptomyces (Morihara and Tsuzuki (1968); Trop and Birk (1968); Wählby and Engström (1968); Wählby (1968; Jurasek et al. (1969)).

The enzyme is synthesized in the pancreas cells of vertebrates as an inactive precursor, trypsinogen, and subsequently converted into the active form by cleavage of the propeptide (Northrop et al. (1948), Desnuelle (1959)). The first trypsinogen molecules were activated naturally by the enteropeptidase enterokinase which hydrolyses the peptide bond between (Asp4)-Lys-⇓-Ile (SEQ ID NO. 25) which cleaves off the propeptide (Keil (1971)). The recognition sequence of the enterokinase (Asp4)-Lys (SEQ ID NO. 24) is accordingly located directly at the C-terminus of the propeptide in almost all previously known trypsinogen molecules (Light et al. (1980)). The activation process can also proceed autocatalytically at physiological pH values since a lysine is located on the C-terminal side of the enterokinase recognition sequence and hence the Lys-⇓-Ile peptide bond can also be hydrolyzed by trypsin (Light et al. (1980)).

Trypsin has always been an interesting protease for biotechnological applications due to its ready availability from various mammals, high specificity (only cleaves at the C-terminal side of lysine or arginine) together with high specific activity (~150 U/mg) and its good storage stability. Trypsin is mainly used for the tryptic cleavage of peptides into small sections for sequencing, for detaching adherent cells from coated cell culture dishes and for cleaving fusion proteins into the target peptide and the fusion component, for activating propeptides (e.g. trypsinogen to trypsin) and for the recombinant production of peptide hormones (e.g. proinsulin to insulin, cf. WO 99/10503). Trypsin is also a component of some pharmaceutical preparations (ointments, dragees and aerosols for inhalation ("Rote Liste", 1997; The United States Pharmacopeia, The National Formulary, USP23-NF18, 1995)). Since the use of enzymes from animal sources is no longer permitted in many cases (potential contamination with infectious agents), recombinant trypsin molecules for the desired biotechnological applications have to be provided from microbial hosts.

There are several methods for the recombinant production of trypsin from various organisms.

Graf, L. et al (1987 and 1988) describe the expression and secretion of rat trypsin and trypsinogen mutants in E. coli. In order to secrete the trypsinogen molecules into the periplasm of E. coli the native trypsinogen signal sequence is replaced by the signal sequence of the bacterial alkaline phosphatase (phoA). The secreted inactive trypsinogen molecules are isolated from the periplasm and activated by enzymatic cleavage using purified enterokinase.

Vasquez, J. R. et al. (1989) describe the expression and secretion of anionic rat trypsin and trypsin mutants in E. coli. In order to express and secrete the active trypsin molecules into the periplasm of E. coli, the native trypsinogen prepro segment (signal sequence and activation peptide) is replaced by the signal sequence of the bacterial alkaline phosphatase (phoA) and the phoA promoter that can be regulated by phosphate is used. Active trypsin is isolated from the periplasm. However, the yield is very low (ca. 1 mg/l).

Higaki, J. N. et al. (1989) describe the expression and secretion of trypsin and trypsin mutants into the periplasm of E. coli using the tac promoter and the S.typhimurium hisJ signal sequence. The yield of active trypsin is ca. 0.3 mg/l. The volume yield of active anionic rat trypsin can be increased to about 50 mg/l by high cell density fermentation (Yee, L. and Blanch, H. W., (1993)). However, the authors refer to problems in the expression and secretion of active trypsin in E. coli. Enzymatically active trypsin is formed in the periplasm of E. coli after cleavage of the signal sequence and native trypsin protein folding to form 6 disulfide bridges. The formation of active trypsin is toxic for the cell since active trypsin hydrolyses the periplasmatic E. coli proteins which lyses the cells. Moreover the protein folding of trypsin and in particular the correct native formation of the 6 disulfide bridges appears to be impeded in the periplasm of E. coli. The system is not suitable for the isolation of relatively large amounts of trypsin (>10 mg; Willett, W. S. et al., (1995)).

In order to produce larger amounts of trypsin (50-100 mg) for X-ray crystallographic investigations, an inactive trypsinogen precursor is produced in yeast under the control of a regulatable ADH/GAPDH promoter and secreted by fusion with the yeast α factor leader sequence. The expression product secreted into the medium is converted quantitatively into trypsin in vitro by means of enterokinase. The yield is 10-15 mg/l (Hedstrom, L. et al. (1992)).

DNA sequences are described in EP 0 597 681 which code for mature bovine trypsin and bovine trypsinogen with an initial methionine residue. In addition the expression in E. coli is described but the strategy of how active trypsin is formed in E. coli is not explained.

A method for producing trypsin from porcine pancreas or a derivative thereof in Aspergillus by a recombinant method is described in WO 97/00316. A vector is used for transformation which codes for trypsinogen or a derivative thereof which is fused at the N-terminus to a functional signal peptide. However, yeast cultures achieve higher biomass concentrations compared to Aspergillus cultures and grow considerably more rapidly and thus the specific expression yield per yeast cell can be less than that for Aspergillus cells in order to achieve yields that are required for an economic expression method.

A method for the recombinant production of a zymogenic precursor of proteases which contains an autocatalytic cleavage site that does not occur naturally is described in WO 99/10503. The method comprises an expression of the zymogenic precursor in *E. coli* in the form of inclusion bodies with subsequent purification and renaturation under conditions where the protease part of the zymogenic precursor is formed in its natural conformation and the cleavage of the renatured zymogenic precursor then occurs autocatalytically. A disadvantage of this method are the large losses that often occur during renaturation and the large volumes that are required for an industrial production.

The recombinant production of trypsin analogues in *Pichia pastoris* is described in WO 00/17332. A vector is used for the transformation which codes for a trypsinogen analogue (derivative of bovine trypsinogen) in which the amino acid lysine at the C-terminus of the propeptide was exchanged by mutation for another amino acid (apart from arginine or lysine) and which is fused N-terminally to a functional signal peptide. In this method the trypsin analogues are secreted into the medium in a soluble form and as a result of the incorporated mutation are also not activated and further degraded by undesired autocatalysis even at relatively high pH values of the fermentation process. An aminopeptidase is then used for activation. However, a disadvantage of this method is the need to remove the additional aminopeptidase which may have disadvantageous side activities for the subsequent use of the trypsin in the final process.

The expression of naturally occurring trypsinogen genes in *Pichia pastoris* is described in WO 01/55429. In order to avoid autocatalytic activation the fermentation is carried out in the example in the less acid pH range at ca. 6. It is thus outside the optimal pH range which prevents autocatalytic activation during longer run times in the expression phase. Other disadvantages of the method are the trypsinogen genes that are not codon-optimized for expression in *Pichia pastoris* and the associated low expression yields.

The object of the invention is to provide a method for the recombinant production of trypsin in which the disadvantages of the prior art are at least partially eliminated and which allows active trypsin to be obtained in a simple manner in a high yield and activity. In particular it should be possible to isolate trypsinogen as an intermediate product in a soluble form from the culture medium of the expression host which should not be subject to any substantial degree of autocatalytic activation during the fermentation and purification. Furthermore it should be possible to subsequently activate the trypsinogen autocatalytically and/or by adding recombinant trypsin.

The object according to the invention is achieved by a method for the recombinant production of trypsin comprising the steps:

a) transforming a host cell with a recombinant nucleic acid which codes for a trypsinogen with an enterokinase recognition site in the propeptide sequence in a secretable form, preferably fused with a signal peptide that mediates secretion, b) culturing the host cell under conditions which enable an expression of the recombinant nucleic acid and a secretion of the expression product into the culture medium, the conditions being selected such that an autocatalytic cleavage of the propeptide sequence is at least substantially prevented, c) isolating the expression product from the culture medium, d) cleaving the propeptide sequence to form active trypsin and e) optionally separating non-cleaved trypsinogen molecules from active trypsin.

The host cell used in the method according to the invention can be a eukaryotic or prokaryotic host cell like those known from the prior art. The host cell is preferably a eukaryotic cell, particularly preferably a fungal cell and most preferably a yeast cell. Suitable examples of yeast cells are *Pichia pastoris, Hansenula polymorpha, Saccharomyces cerevisiae, Schizosaccharomyces pombae* where methylotrophic yeasts such as *Pichia pastoris* or *Hansenula polymorpha* and in particular *Pichia pastoris* are preferably used.

It is expedient to use a host cell that is able to express the recombinant nucleic acid and to secrete the expression product into the culture medium under conditions where an autocatalytic cleavage of the propeptide sequence is at least substantially and preferably essentially quantitatively prevented. Such conditions advantageously comprise an acidic pH value of the culture medium, particularly preferably a pH value in the range between 3 and 4. Trypsinogen is stable at acidic pH values and especially at pH values of up to 4 whereas trypsin is autocatalytically activated in a neutral or alkaline medium (Keil, B. (1971)).

The culture under suitable conditions that occurs in the method according to the invention prevents a premature activation of the recombinant trypsinogen secreted by the host cell which can also substantially prevent further degradation of the resulting trypsin to as far as inactive peptides. The stability of the recombinant trypsinogen under the culture conditions is important since the expression should be accompanied by a secretion. In this connection secretion from the host cell is understood as the discharge of trypsinogen from the cytoplasm through the cell membrane into the culture medium. This usually occurs by N-terminal fusion of the trypsinogen with a functional signal peptide. Examples of suitable signal peptides are known signal peptides from yeast and especially preferably the signal peptide of the a factor from *Saccharomyces cerevisiae*. However, it is of course also possible to use other signal peptides e.g. the signal peptide which naturally controls the secretion of trypsinogen.

In order to improve the expression yield of the recombinant trypsin, a recombinant nucleic acid with an optimized codon usage for the respective host cell is preferably used. Accordingly it is advantageous to use a nucleic acid for a yeast cell which has an optimized codon usage for yeast. Such nucleic acids having an optimized codon usage can for example be produced by synthesizing individual oligonucleotides in parallel and subsequently combining them.

The method according to the invention is basically suitable for producing any types of recombinant trypsin provided the respective trypsinogen that is secreted as an expression product by the host cell is essentially stable under the culture conditions. The method is preferably used to produce trypsin from vertebrates, in particular from mammals such as pigs, sheep or humans. Porcine trypsin is particularly preferably produced.

Furthermore it is preferred that a recombinant nucleic acid is used which codes for a trypsinogen with a shortened propeptide sequence. Trypsinogen is understood as a protein which, although it has formed a substantially correct protein structure, has no or only a very low proteolytic activity compared to active trypsin which is advantageously at least 5-fold and particularly preferably at least 10-fold less than the proteolytic activity of the active form. The natural length of the propeptide part, e.g. 25 amino acids in the case of a porcine trypsinogen, is shortened preferably down to a propeptide sequence which only consists of a recognition sequence for an enteropeptidase e.g. enterokinase e.g. an amino acid sequence Asp-Asp-Asp-Asp-Lys (SEQ ID NO. 24). A few additional amino acids that are due to the cloning, e.g. up to 5 amino acids, can be optionally attached to the N-terminus of the enterokinase recognition sequence.

It was found that the expression of a shortened recombinant trypsinogen according to the invention containing the amino acids Glu-Phe attached due to the cloning to the N-terminus of the enterokinase recognition site results in significantly higher yields than is the case for the expression of natural trypsinogen in the method according to the invention. Hence in a particularly preferred embodiment of the method according to the invention a recombinant nucleic acid having the nucleotide sequence shown in SEQ ID NO.22 is used which codes for a porcine trypsinogen with a shortened propeptide sequence.

In the method according to the invention the expression of the recombinant trypsinogen is preferably controlled by an inducible expression control sequence. Hence the growth of the host cell can take place before induction of expression under conditions which are favourable or optimal for the growth of the host cell. Thus for example growth can take place at pH 5-7, in particular pH 5-6 up to a predetermined optical density during which the regulatable expression control sequence is repressed. Expression can then be induced by changing the temperature and/or by adding an inducer. An example of a preferred expression control sequence is the AOX 1—promoter from *Pichia pastoris* that can be induced by methanol which is particularly suitable for inducible expression in methylotrophic yeasts. The culture conditions are advantageously changed before induction of the expression control sequence in such a manner that for example by changing the pH to a range of 3-4 the trypsinogen formed by expression of the recombinant nucleic acid accumulates in an intact form in the culture medium.

The culture conditions in the method according to the invention are selected such that autocatalytic cleavage of the propeptide sequence is substantially prevented. After isolating the expression product from the culture medium, the propeptide sequence can be cleaved off under controlled conditions. This cleavage can for example be carried out by adding recombinant trypsin or/and by autocatalytic cleavage. In this connection autocatalytic cleavage is understood as the self-activation of recombinant trypsinogen which may be optionally accelerated by adding small amounts of recombinant trypsin but without adding a foreign protein. In this manner it is not necessary to use an additional foreign protein which is usually derived from animal raw material sources and has to be subsequently removed again which could cause undesired cleavages in the subsequent application. The autocatalytic activation preferably occurs at a pH in the range of 7-8. This ensures that the trypsinogen formed during the expression can be firstly highly purified in a strongly acidic range and the activation can be specifically started by rebuffering preferably in the presence of small amounts e.g. 20 mM $CaCl_2$ to a neutral to weakly basic pH range. The activation can be stopped by changing the pH again to a strongly acidic range. Trypsin can for example be purified by chromatography on ion exchanger material such as SP-Sepharose®XL or benzamidine-Sepharose.

In order to purify the expression product from the culture medium, the culture supernatant can be firstly separated from the cells as described in example 6.1. The subsequent purification comprising an autocatalytic activation of the trypsinogen is preferably carried out by suitable chromatographic purification procedures. In a particularly preferred embodiment a chromatography is carried out as described in example 6.2. without prior separation of the cells in which a buffer containing calcium ions preferably at a final concentration of 1-30 mM calcium is added to the culture medium which still contains the cells. Subsequently steps (c), (d) and optionally (e) of the method according to the invention are carried out for example using suitable chromatographic purification procedures and a rebuffering step for the autocatalytic cleavage of the expression product.

Hence a particularly preferred embodiment of the method according to the invention is characterized by:

a) transforming a host cell with a recombinant nucleic acid which codes for the zymogenic precursor trypsinogen from the pig which is fused with a signal peptide sequence and contains a propeptide which is shortened down to the enterokinase recognition sequence, where this cleavage site is cleaved by recombinant trypsin or is autocatalytically cleaved under certain buffer conditions and the shortened trypsinogen can be cleaved to form active trypsin in this process, b) culturing the host cell during the expression phase at an acidic pH, preferably pH 3-4 so that the shortened trypsinogen is present in a soluble form and secreted into the culture medium but the autocatalytic activation is substantially prevented, c) isolating the shortened recombinant trypsinogen from the culture supernatant and activating it under conditions which allow an effective cleavage of the shortened trypsinogen by recombinant trypsin or by autocatalytic cleavage and d) optionally separating non-cleaved trypsinogen molecules from active trypsin.

The shortening of the propeptide described in this invention has a positive effect especially on expression and autocatalytic activation. Furthermore after the autocatalytic activation, the undesired further autolysis increases significantly at a pH of >4.0 during the growth phase and expression phase of the culture.

An additional increase in the expression yield in the method according to the invention can be achieved by transforming the host cell with several vectors each of which contains a recombinant nucleic acid as stated above where the vectors contain different selection markers e.g. Zeocin and G418. Culture under multiple selection conditions surprisingly allows the expression yield of recombinant trypsinogen to be increased considerably further.

Another subject matter of the invention is a recombinant nucleic acid which codes for a trypsinogen having an enterokinase recognition site in the propeptide sequence where the propeptide sequence is shortened relative to the natural propeptide sequence and is preferably fused with a signal peptide sequence. The shortened propeptide sequence according to the invention preferably consists of an enterokinase recognition site having the amino acid sequence Asp-Asp-Asp-Asp-Lys (SEQ ID NO. 24) and optionally up to 5 additional amino acids located arranged N-terminally thereof. The nucleic acid according to the invention particularly preferably has the nucleotide sequence shown in SEQ ID NO.22.

The nucleic acid according to the invention is preferably in operative linkage with a regulatable expression control sequence which is for example a suitable expression control sequence for gene expression in yeast cells such as the AOX1 promoter from *Pichia pastoris*.

The invention also concerns a recombinant vector which contains at least one copy of a recombinant nucleic acid as stated above. The vector is preferably a vector that is suitable for gene expression in yeast cells. Examples of such vectors are described in Sambrook et al., Molecular cloning: A Laboratory Manual, Cold Spring Harbor Laboratory Press, Cold Spring Harbor, N.Y.

In addition to the recombinant nucleic acid, the vector contains other suitable genetic elements for the respective intended use and in particular a selection marker gene. Vectors are particularly preferably used which can be present in the cell in multiple copies especially vectors which can be integrated in a multiple form into the genome of the host cell. The invention also concerns combinations of vectors which each contain different selection marker genes and which can be propagated concurrently in a host cell.

In addition the invention concerns a recombinant cell which is transformed with a nucleic acid according to the invention or a vector according to the invention. The recombinant cell is preferably a yeast cell in particular a methylotrophic yeast cell such as *Pichia pastoris* or *Hansenula polymorpha*.

Finally the invention concerns a recombinant trypsinogen which is coded by a nucleic acid according to the invention. The recombinant trypsinogen has a propeptide sequence which is shortened compared to the natural propeptide sequence and contains an enterokinase recognition site. The recombinant trypsinogen according to the invention preferably has the amino acid sequence shown in SEQ ID NO. 23.

The present invention is also elucidated by the following figures and examples.

FIG. 1: shows a plasmid map of the expression plasmid pTRYP-9 containing the complete recombinant trypsinogen, FIG. 2: shows a plasmid map of the expression plasmid pTRYP-11 containing the shortened recombinant trypsinogen (sh-trypsinogen) and the Zeocin resistance marker gene (ZeoR), FIG. 3: shows a plasmid map of the expression plasmid pTRYP-13 containing the shortened recombinant trypsinogen (sh-trypsinogen) and a kanamycin/G418 selection marker gene (KanR).

EXAMPLES

Methods:

Recombinant DNA Techniques

Standard methods were used to manipulate DNA as described by Sambrook, J. et al. (1989) in Molecular Cloning: A Laboratory Manual. Cold Spring Harbor Laboratory Press, Cold Spring Harbor, N.Y. The molecular biological reagents were used according to the manufacturer's instructions.

Protein Determination

The protein determination of purified trypsin was carried out by measuring the absorbance at 280 nm. A value of 13.6 was used for A 1%/280 nm for 1 cm path length.

Calculation:

Protein [mg/ml]=(10 [mg/ml]*$\Delta A_{sample}$*dilution)/13.6

*Pichia pastoris* and Expression Vectors for *Pichia pastoris*

The catalogue and instruction manuals from Invitrogen were used as instructions for handling *Pichia pastoris* and the expression vectors. The vectors for expressing the shortened recombinant trypsinogen are based on the vectors pPICZαA and pPIC9K from Invitrogen.

Example 1

Gene synthesis of the complete recombinant trypsinogen with optimized codon usage for expression in yeast One of the preferred methods for providing the method according to the invention is to synthesize a codon-optimized gene sequence. In order to optimize each codon for expression in yeast it was necessary to carry out a complete de novo synthesis of the ca. 700 bp gene which codes for the complete recombinant trypsinogen. It was possible to optimize each codon when necessary by utilizing the degenerate code in the retranslation of the amino acid sequence of porcine trypsinogen according to SEQ ID NO.1. For this purpose the gene was divided into 18 oligonucleotides having a length of 54 to 90 nucleotides. The oligonucleotides were designed as an alternating sequence of sense strand and counter-strand fragments whose 5' and 3' ends each overlapped in a complementary manner with the neighboring oligonucleotides. The overlapping region was selected in each case such that unspecific binding was largely prevented in the annealing reaction in the subsequent PCR reaction. The oligonucleotides at the 5' and 3' end of the gene were provided upstream and downstream of the coding region with recognition sites for restriction endonucleases which could be used for the later insertion of the synthetic gene according to SEQ ID NO.2 into expression vectors. Thus a recognition site for the restriction endonuclease EcoRI was incorporated upstream and a recognition site for the restriction endonuclease XbaI was incorporated downstream. The sequences of the oligonucleotides are shown in SEQ ID NO.3 to 20.

Gene synthesis was carried out by means of the PCR reaction. For this the coding region was firstly divided into three segments (oligonucleotides 3 to 8, 9 to 14, 15 to 20) and these segments were generated in separate PCR reactions using overlapping complementary oligonucleotides. In this process the gene fragment was extended in a stepwise manner till the full length product was formed which was then amplified in subsequent cycles. The annealing temperature was selected according to the overlapping region with the lowest melting temperature.

The three segments were subsequently analysed by agarose gel electrophoresis, the products having the expected length were isolated from the gel by means of the QIAquick Gel Extraction Kit (Qiagen) and synthesized to form the complete gene product in a further PCR reaction. The first 5 cycles of the PCR reaction were carried out without adding the primer at the 5' end and at the 3' end of the entire gene so that at first a few fragments of the gene product of the expected length were formed from the three segments. The annealing temperature was selected according to the overlapping region with the lowest melting temperature. Then the terminal primers were added and the annealing temperature was increased according to the annealing temperature of the primer with the lowest melting temperature. The gene fragment of the expected length was then amplified in a further 25 cycles. The PCR fragment was checked by sequencing.

Example 2

Generation of the Shortened Trypsinogen Gene

The codons for the first 20 amino acids of the naturally occurring trypsinogen were deleted by means of a specially designed 5' primer according to SEQ ID NO. 21 such that only the codons for the recognition sequence of the enteropeptidase enterokinase Asp-Asp-Asp-Asp-Lys (SEQ ID NO. 24) and the codons Glu-Phe necessary for cloning into the expression vectors for *Pichia pastoris* due to the EcoRI restriction endonuclease recognition sequence remain as the sequence of the propeptide at the N-terminus of the shortened recombinant trypsinogen. The deletion was introduced by a PCR reaction on the PCR fragment of the gene for the complete recombinant trypsinogen using the 5' primer according to SEQ ID NO. 21 and the 3' primer according to SEQ ID NO. 20. The DNA sequence and the amino acid sequence of the shortened recombinant trypsinogen are shown in SEQ ID NO. 22 and SEQ ID NO. 23 respectively.

Example 3

Cloning the PCR Fragments of the Complete Recombinant Trypsinogen Generated by Gene Synthesis and of the Shortened Recombinant Trypsinogen into Expression Vectors for *Pichia pastoris*

The PCR fragments were recleaved with EcoRI and XbaI (Roche Diagnostics GmbH), isolated again (QIAquick Gel Extraction Kit/Qiagen) and subsequently ligated into a fragment of the expression vector pPICZαA (Invitrogen) linearized with EcoRI and XbaI (Roche Diagnostics GmbH) and isolated with the QIAquick Gel Extraction Kit/Qiagen. For this 1 µl (20 ng) vector fragment and 3 µl (100 ng) PCR fragment, 1 µl 10× ligase buffer (Sambrook et al., 1989 B.27), 1 µl T4 DNA ligase, 4 µl sterile $H_2O_{redistilled}$ were pipetted, carefully mixed and incubated overnight at 16° C. In this vector the synthetic gene is under the control of the AOX 1 promoter (promoter for the alcohol oxidase 1 from *Pichia pastoris*) that can be induced with methanol (Mallinckrodt Baker B.V.) and is located in the correct reading frame behind the signal peptide of the a factor from *Saccharomyces cerevisiae*. In order to check this and isolate the plasmid, 5 µl of the ligation mixture were then transformed in 200 µl competent cells (Hanahan (1983) of *E. coli* XL1Blue (Stratagene). A 30 min incubation on ice was followed by a heat shock (90 sec at 42° C.). Subsequently the cells were transferred to 1 ml LB medium and incubated for 1 hour at 37° C. in LB medium for phenotypic expression. Aliquots of this transformation mixture were plated out on LB plates using 100 µg/ml Zeocin as the selection marker and incubated for 15 hours at 37° C. The plasmids were isolated from the grown clones (Sambrook, J. et al. (1989) In. Molecular cloning: A Laboratory Manual. Cold Spring Harbor Laboratory Press, Cold Spring Harbor, N.Y.) and then checked for an error-free base sequence by means of restriction analysis and sequencing. The expression vectors formed in this manner which contain a synthetic gene for the complete recombinant trypsinogen or a shortened recombinant trypsinogen were named pTRYP-9 (see FIG. 1) and pTRYP-11 (see FIG. 2).

Transformation of pTRYP-9 and pTRYP-11 into *Pichia pastoris*

For the transformation of pTRYP-9 and pTRYP-11 into *Pichia pastoris* X-33, GS 115 or KM71H with subsequent integration into the genome, the vector was firstly linearized with SacI (Roche Diagnostics GmbH). The transformation was carried out by electroporation using the Gene Pulser II (Biorad). For this a colony of *Pichia pastoris* was inoculated with 5 ml YPD medium (Invitrogen) and incubated overnight at 30° C. while shaking. The overnight culture was subsequently reinoculated 1:2000 in 200 ml fresh YPD medium (Invitrogen) and incubated overnight at 30° C. while shaking until an $OD_{600}$ of 1.3 to 1.5 was reached. The cells were centrifuged (1500×g/5 minutes) and the pellet was resuspended in 200 ml ice-cold, sterile water (0° C.). The cells were again centrifuged (1500×g/5 minutes) and resuspended in 100 ml ice-cold, sterile water (0° C.). The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells isolated in this manner were kept on ice and immediately used for the transformation.

80 µl of the cells were admixed with ca. 1 µg linearized pTRYP-9 or pTRYP-11 vector DNA and the entire mixture was transferred into an ice-cold (0° C.) electroporation cuvette and incubated for a further 5 minutes on ice. Subsequently the cuvette was placed in the Gene Pulser II (Biorad) and transformation was carried out at 1 kV, 1 kΩ and 25 µF. After electroporation the mixture was admixed with 1 ml 1 M sorbitol (ICN) and subsequently 100 to 150 µl was plated out on a YPDS agar plate (Invitrogen) containing 100 µg/ml Zeocin (Invitrogen). The plates were subsequently incubated for 2-4 days at 30° C.

The clones were reinoculated on raster MD (=minimal dextrose) plates and analysed further. Grown clones were picked, resuspended in 20 µl sterile water, lysed (1 hour, 30° C., 10 min, −80° C.) with 17.5 U lyticase (Roche Diagnostics GmbH) and directly examined for correct integration of the synthetic trypsinogen expression cassette by means of PCR.

Clones which had integrated the complete expression cassette during transformation into the genome, were then used in expression experiments.

Expression of the Complete and Shortened Recombinant Trypsinogen

Positive clones were inoculated in 3 ml BMGY medium (Invitrogen) and incubated overnight at 30° C. while shaking. Subsequently the OD was determined at 600 nm and they were reinoculated in 10 ml BMMY medium (Invitrogen) pH 3.0 such that the resulting $OD_{600}$ was 1. The BMMY medium (Invitrogen) pH 3.0 contains methanol (Mallinckrodt Baker B.V.) which induces the expression of the complete or shortened recombinant trypsinogen via the AOX1 promoter.

The shaking flasks were incubated at 30° C. while shaking, samples were taken every 24 hours, the $OD_{600}$ was determined, an aliquot was taken to check the expression of the complete and shortened recombinant trypsinogen by means of SDS polyacrylamide gel electrophoresis and each was supplemented with 0.5% methanol (Mallinckrodt Baker B.V.) for further induction. The expression experiments were carried out for 72 hours.

Analysis of the Expression of the Complete and Shortened Recombinant Trypsinogen by Means of SDS Gel Electrophoresis 500 µl were taken from each expression culture, the $OD_{600}$ was determined and the cells were centrifuged. The culture supernatant was stored and the cell pellet was resuspended for the lysis in an appropriate amount of Y-PER™ (50 to 300 µl/Pierce) for the $OD_{600}$ and shaken for 1 hour at room temperature. Subsequently the lysate was centrifuged to separate cell debris (15000×g/5 minutes) and the supernatant was transferred to fresh reaction vessels. 10 µl lysate and 10 µl of the culture supernatant were applied to an SDS polyacrylamide gel and the proteins were separated according to size by applying an electrical field.

Surprisingly it was possible to identify weak bands in the culture supernatants of clones containing the complete recombinant trypsinogen as well as of clones containing the shortened recombinant trypsinogen that did not occur in the control clones. Control clones are to be understood as *Pichia pastoris* X33 cells that have been transformed with the starting vector pPICZαA and that have been grown and induced analogously to the expression clones for trypsinogen. The migration properties of the new protein bands in the expression clones corresponds to the calculated molecular weight and is slightly higher than that of bovine trypsin that had been applied as the control marker. This slight difference in size indicates an intact, non-activated trypsinogen.

Surprisingly the recombinant shortened trypsinogen was expressed significantly more strongly than the recombinant complete trypsinogen.

Example 4

Increasing the Expression Yield by Multiple Transformation

The best clones from the expression experiments with the recombinant shortened trypsinogen were again prepared for electroporation as described above and again transformed with 1 µg linearized pTRYP-11 vector DNA and the transformation mixture was plated out on YPDS agar plates (Invitrogen) containing 1000 to 2000 µg/ml Zeocin (Invitrogen). This increases the selection pressure in such a way that only clones can grow that have integrated several copies of the expression vector pTRYP-11 into the genome and hence also several copies of the respective resistance gene (in this case Zeocin®). The Zeocin® resistance protein is the product of the bleomycin gene from *Streptoalloteichus hindustanus* (Calmels, T. et al., (1991); Drocourt, D. et al., (1990)), which binds Zeocin® in a stoichiometric concentration ratio and hence makes the cell resistant to Zeocin®. The higher the concentration of Zeocin® in the YPDS agar plates, the more resistance protein has to be produced by the cell in order to quantitatively bind Zeocin® and thus allow growth. This is among others possible when multiple copies of the resistance gene are integrated into the genome. Clones were reinoculated on raster MD plates as described above. Subsequently these clones were in turn checked for trypsinogen expression and secretion as described above.

Surprisingly it was possible after this measure to identify clones having considerably increased expression yield of the shortened recombinant trypsinogen secreted into the culture supernatant after SDS polyacrylamide gel electrophoresis.

Example 5

Increasing the Expression Yield by Using a Second Selection Pressure

Increasing the Zeocin® concentration above 2000 µg/ml did not lead to an improved expression yield of the shortened recombinant trypsinogen. In order to further increase the gene copy number in the expression clones of the gene according to SEQ ID NO. 22 which codes for the recombinant shortened trypsinogen and is codon-optimized for expression in yeast, additional expression vectors were integrated into the genome of the expression clones prepared in examples 3 and 4 having the highest expression yield by means of a second selection pressure, preferably G418 (Roche Diagnostics GmbH).

For this purpose a part of the expression cassette from pTRYP-11 consisting of a part of the AOX1 promoter, the gene for the signal peptide of the α factor of *Saccharomyces cerevisiae*, the codon-optimized gene for the recombinant shortened trypsinogen according to SEQ ID NO.22, is cut out with the restriction endonucleases SacI and XbaI from pTRYP-11, the restriction mixture is separated on a 1% agarose gel and the 1693 bp fragment is isolated from the gel (QIAquick Gel Extraction Kit/Qiagen). At the same time the vector pPIC9K (Invitrogen) was cleaved with SacI and NotI, the restriction mixture was separated on a 1% agarose gel and the 8956 bp vector fragment was isolated from the gel (QIAquick Gel Extraction Kit/Qiagen). The XbaI overhang of the fragment from pTRYP-11 and the NotI overhang from pPIC9K was filled up with Klenow polymerase (Roche Diagnostics GmbH) to form blunt ends according to the manufacturer's instructions. Subsequently the two fragments obtained in this manner were ligated as described above. The ligation mixture was transformed in *E. coli* XL1 Blue (Stratagene) as described above (the clones containing plasmid were selected by 100 µg/ml ampicillin in the nutrient plates) and checked by means of restriction analysis and sequencing. The expression vector formed in this way was named pTRYP-13 (see FIG. 3).

The integration of the expression vector pTRYP-13 into the genome of *Pichia pastoris* was selected by means of G418 (Roche Diagnostics GmbH).

The clones having the highest trypsinogen expression yield from the multiple transformation with pTRYP-11 (Zeocin resistance) were prepared for electroporation as described above and transformed with 1 µg of the vector fragment from pTRYP-13 (G418 resistance) linearized with SalI (Roche Diagnostics GmbH). The transformation mixture was subsequently stored for 1 to 3 days at 4° C. in 1 M sorbitol (ICN) (for the formation of G418 resistance), then 100 to 200 µl was plated out on YPD plates (Invitrogen) containing 1, 2 and 4 mg/ml G418 (Roche Diagnostics GmbH) and incubated for 3 to 5 days at 30° C. The clones resulting therefrom preferably from the YPD plates with the highest G418 concentration, were again examined for an increased expression of the shortened recombinant trypsinogen using SDS polyacrylamide gel electrophoresis as described above.

After this process is was surprisingly possible to again identify clones having an increased expression yield of the shortened recombinant trypsinogen in the culture supernatant after SDS polyacrylamide gel electrophoresis.

Example 6

Isolating Trypsinogen From the Culture Supernatant and Activation 6.1

The culture supernatant was separated from the cells by microfiltration, centrifugation or filtration. The trypsinogen was purified by chromatography on phenyl Sepharose fast flow (Pharmacia). The chromatography was carried out in a pH range of 2-4. Autocatalytic activation was started by rebuffering the pH to 7-8 in the presence of 20 mM $CaCl_2$. This autocatalytic activation can be terminated again by changing the pH back into the range of 2-4. Active trypsin was purified by chromatography on benzamidine Sepharose (e.g. SP-Sepharose®XL, ff) (Pharmacia/package insert) or on an ion exchanger. Trypsin is stored at pH 1.5-3 in order to avoid autolysis. The specific activity of the purified trypsin is 180-200 U/mg protein.

6.2

The entire fermentation broth is diluted in a ratio of about 1:2 to 1:4 with ammonium acetate buffer (5-20 mM) containing 5-30 mM calcium chloride, pH 3.5 and purified by means of an expanded bed chromatography (McCornick (1993); EP 0 699 687) using a cation exchanger (e.g. Streamline®SP, XL). In this case the chromatography is carried out in the presence of the cells. The cells are simultaneously separated by the chromatography step. Subsequently the procedure is as described in example 6.1 (rebuffering/activation etc.).

Example 7

Activity Determination

The activity of trypsin was determined using Chromozym TRY (Pentapharm Ltd) in 100 mM Tris pH 8.0, 20 mM $CaCl_2$ at 25° C. The photometric measurement is carried out at 405 nm.

Abbreviations:

| | |
|---|---|
| YPD: | yeast peptone dextrose |
| YPDS: | yeast peptone dextrose sorbitol |
| BMGY: | buffered glycerol-complex medium |
| BMMY: | buffered methanol-complex medium |
| SDS: | sodium dodecyl sulfate |

LIST OF LITERATURE REFERENCES

Bricteuz-Gregoire, Schyns R., Florkin M (1966) Biochim. Biophys. Acta 127: pp 277.
Calmels T., Parriche M., Durand H., Tiraby G. (1991), Curr. Genet. 20: pp 309.
Charles M., Rovery M., Guidoni A., Desnuelle P. (1963) Biochim. Biophys. Acta 69: pp 115-129.
Desnuelle P. (1959) The Enzymes $2^{nd}$ Edition vol 4 Editor Boyer, Acad. Press NY. pp. 119.
Drocourt, D., Calmels T., Reynes J. P., Baron M., Tiraby G. (1990), Nucleic Acid Research 18: pp 4009.
Graf L., Craik C. S., Patthy A., Roczniak S., Fletterick R J., Rutter W. J. (1987) Biochem. 26: pp. 2616.
Graf L., Jancso A., Szilagyi L., Hegyi G., Pinter K., Naray-Szabo G., Hepp J., Mehzihradszky K., Rutter W. J. (1988) Proc. Natl. Acad. Sci USA 85, pp 4961.
Hanahan (1983) J. Mol. Biol., 166: pp 557.
Higaki J. N., Evnin L. B., Craik C. S. (1989) Biochem. 28: pp 9256.
Hedstrom L., Szilagyi L., Rutter W. J. (1992) Science 255: pp 1249.
Jurasek L., Fackre D. Smillie L. B. (1969) Biochem. Biophys. Res. Commun 37: pp. 99.
Keil B. (1971) The Enzymes Vol II, $3^{rd}$ Edition, Editor Boyer, Acad. Press N.Y. pp 249-275.
Light A., Savithari H. S., Liepnieks J. J. (1980) Analytical Biochemistry 106: pp 199-206.
McComick, D. K., Bio/Technol. 11 (1993), 1059; Expanded Bed Absorption, Principles and Methods, Amersham Pharmacia Biotech, Edition AB, ISBN 91-630-5519-8.
Morihara K. and Tszzuki J. (1969) Arch Biochem Biophys 126: pp 971.
Northrop J. H., Kunitz M., Herriott R. (1948) Crystalline Enzymes, $2^{nd}$ Edition, Columbia Univ. Press NY.
Ryan C. A. (1965) Arch Biochem Biophys 110: pp 169.
Sambrook, J., Fritsch E. F., Maniatis T. (1989) In. Molecular Cloning: A Laboratory Manual. Cold Spring Harbor Laboratory Press, Cold Spring Harbor, N.Y.
Travis J. (1968) Biochem Biophys Res Commun. 30: pp 730.
Travis J. and Roberts R. C. (1969) Biochemistry 8: pp 2884.
Trop M. and Birk Y. (1968) Biochem. J. 109: pp 475.
Wählby S. and Engström L. (1968) Biocheim. Biophys. Acta 151: pp 402.
Vasquez, J. R. Evnin L. B., Higaki J. N. Craik C. S. (1989) J. Cell. Biochem. 39: pp. 265.
Wählby S. (1968) Biochim. Biophys. Acta 151: pp 394.
Willett, W. S., Gillmor S. A., Perona J. J., Fletterick R. J., Craik C. S. (1995) Biochem. 34: pp 2172.
Yee, L. and Blanch, H. W., (1993) Biotechnol. Bioeng. 41: pp. 781-790.
WO 97/00316 (NOVO NORDISK AS/Wöldike Helle, Kjeldsen Thomas) A PROCESS FOR PRODUCING TRYPSIN.
WO 99/10503 (ROCHE DIAGNOSTICS/Kopetzki Ehrhard, Hopfner Karl-Peter, Bode Wolfram, Huber Robert) ZYMOGENIC PROTEASE PRECURSOR THAT CAN BE AUTOCATALYTICALL ACTIVATED AND THEIR USE.
WO 00/17332 (ELI LILLY AND COMPANY/Hanquier Jose Michael, Hershberger Charles Lee, Desplancq Dominique, Larson Jeffrey) PRODUCTION OF SOLUBLE RECOMBINANT TRYPSINOGEN ANALOGS.
WO 01/55429 (POLYMUN SCIENTIFIC IMMUNBIOLOGISCHE FORSCHUNG GMBH/Mattanovich Diethard, Katinger Hermann, Hohenblum Hubertus, Naschberger Stefan, Weik Robert) METHOD FOR THE MANUFACTURE OF RECOMBINANT TRYPSIN.
EP 0 597 681 (ELI LILLY AND COMPANY/Greaney Michael Gerard, Rostech Paul Robert) EXPRESSION VECTORS FOR THE BOVINE TRYPSIN AND TRYPSINOGEN AND HOST CELLS TRANSFORMED THEREWITH.
EP 0 699 687 (MITSUBISHI PHARMA CORPORATION/Noda Munehiro, Sumi Akinori, Ohmura Takao, Yokoyama Kazmasa) PROCESS FOR PURIFYING RECOMBINANT HUMAN SERUM ALBUMIN.

The invention claimed is:

1. A trypsinogen protein consisting of a first amino acid sequence and a second amino acid sequence, wherein the C-terminus of the first amino acid sequence is bound directly to the N-terminus of the second amino acid sequence, said first amino acid sequence consisting of the amino acid sequence set forth in SEQ ID NO:26 and said second amino acid sequence consisting of a trypsin amino acid sequence.

2. The trypsinogen protein of claim 1 wherein said trypsin amino acid sequence is a porcine trypsin amino acid sequence.

3. A trypsinogen protein comprising the amino acid sequence shown in SEQ ID NO:27.

4. A trypsinogen protein produced by the steps comprising
   a) preparing a yeast host cell comprising a recombinant nucleic acid that encodes a trypsinogen protein comprising a signal peptide, the C-terminus of which is bound directly to the N-terminus of the shortened propeptide amino acid sequence set forth in SEQ ID NO:26, the C-terminus of which is bound directly to the N-terminus of a trypsin amino acid sequence, wherein said signal peptide mediates secretion of trypsinogen from the host cell,
   b) culturing the yeast host cell in a first culture medium under conditions promoting the growth of the yeast host cell;
   c) culturing the yeast host cell in a second culture medium having a pH of from 3.0 to 4.0 and inducing the expression of said recombinant nucleic acid, whereby the yeast host cell expresses trypsinogen comprising the shortened propeptide in the second culture medium significantly more than trypsinogen comprising a complete propeptide, and
   d) isolating the trypsinogen comprising the propeptide from the second culture medium.

* * * * *

SEQUENCE LISTING

```
<160> NUMBER OF SEQ ID NOS: 27

<210> SEQ ID NO 1
<211> LENGTH: 247
<212> TYPE: PRT
<213> ORGANISM: Porcine

<400> SEQUENCE: 1

Ile Pro Asn Thr Phe Val Leu Leu Ala Leu Leu Gly Ala Ala Val Ala
1               5                   10                  15

Phe Pro Thr Asp Asp Asp Lys Ile Val Gly Gly Tyr Thr Cys Ala
            20                  25                  30

Ala Asn Ser Ile Pro Tyr Gln Val Ser Leu Asn Ser Gly Ser His Phe
        35                  40                  45

Cys Gly Gly Ser Leu Ile Asn Ser Gln Trp Val Val Ser Ala Ala His
    50                  55                  60
```

```
Cys Tyr Lys Ser Arg Ile Gln Val Arg Leu Gly Glu His Asn Ile Asp
 65                  70                  75                  80

Val Leu Glu Gly Asn Glu Gln Phe Ile Asn Ala Ala Lys Ile Ile Thr
                 85                  90                  95

His Pro Asn Phe Asn Gly Asn Thr Leu Asp Asn Asp Ile Met Leu Ile
            100                 105                 110

Lys Leu Ser Ser Pro Ala Thr Leu Asn Ser Arg Val Ala Thr Val Ser
        115                 120                 125

Leu Pro Arg Ser Cys Ala Ala Ala Gly Thr Glu Cys Leu Ile Ser Gly
    130                 135                 140

Trp Gly Asn Thr Lys Ser Ser Gly Ser Ser Tyr Pro Ser Leu Leu Gln
145                 150                 155                 160

Cys Leu Lys Ala Pro Val Leu Ser Asp Ser Ser Cys Lys Ser Ser Tyr
                165                 170                 175

Pro Gly Gln Ile Thr Gly Asn Met Ile Cys Val Gly Phe Leu Glu Gly
            180                 185                 190

Gly Lys Asp Ser Cys Gln Gly Asp Ser Gly Gly Pro Val Val Cys Asn
        195                 200                 205

Gly Gln Leu Gln Gly Ile Val Ser Trp Gly Tyr Gly Cys Ala Gln Lys
    210                 215                 220

Asn Lys Pro Gly Val Tyr Thr Lys Val Cys Asn Tyr Val Asn Trp Ile
225                 230                 235                 240

Gln Gln Thr Ile Ala Ala Asn
                245

<210> SEQ ID NO 2
<211> LENGTH: 744
<212> TYPE: DNA
<213> ORGANISM: Artificial Sequence
<220> FEATURE:
<223> OTHER INFORMATION: Synthetic gene

<400> SEQUENCE: 2
attccaaata cttttgtttt gttggctttg ttgggtgctg ctgttgcttt tccaactgat      60
gatgatgata aaattgttgg tggttatact tgtgctgcta attctattcc atatcaagtt     120
tctttaaatt ctggttctca tttttgtggt ggttctttga ttaattctca atgggttgtt     180
tctgctgctc attgttacaa atcaagaatc caagttagat gggtgaaca taatattgat     240 gttttggaag gtaatgaaca atttattaat gctgctaaaa ttattactca tccaaatttt     300
aatggtaata ctttggataa tgatattatg ttgattaaat tgtcttctcc agctacttta     360
aattcaagag ttgctactgt ttctttgcca agatcttgtg ctgctgctgg tactgaatgt     420
ttgatttctg gttggggtaa tactaaatct tctggttctt cttatccatc tttgttgcaa     480
tgtttgaaag ctccagtttt gtctgattct tcttgtaaat cttcttaccc aggtcaaatt     540
actggtaata tgatttgtgt tggttttttg gaaggtggta agattcttg tcaaggtgat     600 tctggtggtc cagttgtttg taatggtcaa ttgcaaggta ttgtttcttg gggttatggt     660
tgtgctcaaa aaataaaacc aggtgtttac actaaagttt gtaattatgt taattggatt     720
caacaaacta ttgctgctaa ttag                                             744

<210> SEQ ID NO 3
<211> LENGTH: 56
<212> TYPE: DNA
<213> ORGANISM: Artificial Sequence
<220> FEATURE:
<223> OTHER INFORMATION: primer
```

<400> SEQUENCE: 3
gcggaattca ttccaaatac ttttgttttg ttggctttgt tgggtgctgc tgttgc        56

<210> SEQ ID NO 4
<211> LENGTH: 54
<212> TYPE: DNA
<213> ORGANISM: Artificial Sequence
<220> FEATURE:
<223> OTHER INFORMATION: primer

<400> SEQUENCE: 4
ccaccaacaa ttttatcatc atcatcagtt ggaaaagcaa cagcagcacc caac          54

<210> SEQ ID NO 5
<211> LENGTH: 62
<212> TYPE: DNA
<213> ORGANISM: Artificial Sequence
<220> FEATURE:
<223> OTHER INFORMATION: primer

<400> SEQUENCE: 5
gatgataaaa ttgttggtgg ttatacttgt gctgctaatt ctattccata tcaagtttct    60
tt                                                                   62

<210> SEQ ID NO 6
<211> LENGTH: 64
<212> TYPE: DNA
<213> ORGANISM: Artificial Sequence
<220> FEATURE:
<223> OTHER INFORMATION: primer

<400> SEQUENCE: 6
gaattaatca agaaccacc acaaaaatga gaaccagaat ttaaagaaac ttgatatgga     60
atag                                                                 64

<210> SEQ ID NO 7
<211> LENGTH: 64
<212> TYPE: DNA
<213> ORGANISM: Artificial Sequence
<220> FEATURE:
<223> OTHER INFORMATION: primer

<400> SEQUENCE: 7
ggtggttctt tgattaattc tcaatgggtt gtttctgctg ctcattgtta caaatcaaga    60
atcc                                                                 64

<210> SEQ ID NO 8
<211> LENGTH: 62
<212> TYPE: DNA
<213> ORGANISM: Artificial Sequence
<220> FEATURE:
<223> OTHER INFORMATION: primer

<400> SEQUENCE: 8
ccttccaaaa catcaatatt atgttcaccc aatctaactt ggattcttga tttgtaacaa    60
tg                                                                   62

<210> SEQ ID NO 9
<211> LENGTH: 63
<212> TYPE: DNA
<213> ORGANISM: Artificial Sequence
<220> FEATURE:

<223> OTHER INFORMATION: primer

<400> SEQUENCE: 9
taatattgat gttttggaag gtaatgaaca atttattaat gctgctaaaa ttattactca    60
tcc                                                                  63

<210> SEQ ID NO 10
<211> LENGTH: 62
<212> TYPE: DNA
<213> ORGANISM: Artificial Sequence
<220> FEATURE:
<223> OTHER INFORMATION: primer

<400> SEQUENCE: 10
caacataata tcattatcca agtattacc attaaaattt ggatgagtaa taattttagc    60
ga                                                                   62

<210> SEQ ID NO 11
<211> LENGTH: 64
<212> TYPE: DNA
<213> ORGANISM: Artificial Sequence
<220> FEATURE:
<223> OTHER INFORMATION: primer

<400> SEQUENCE: 11
ctttggataa tgatattatg ttgattaaat tgtcttctcc agctacttta aattcaagag    60
ttgc                                                                 64

<210> SEQ ID NO 12
<211> LENGTH: 58
<212> TYPE: DNA
<213> ORGANISM: Artificial Sequence
<220> FEATURE:
<223> OTHER INFORMATION: primer

<400> SEQUENCE: 12
ccagcagcag cacaagatct tggcaaagaa acagtagcaa ctcttgaatt taaagtag      58

<210> SEQ ID NO 13
<211> LENGTH: 61
<212> TYPE: DNA
<213> ORGANISM: Artificial Sequence
<220> FEATURE:
<223> OTHER INFORMATION: primer

<400> SEQUENCE: 13
cttgtgctgc tgctggtact gaatgtttga tttctggttg gggtaatact aaatcttctg    60
g                                                                    61

<210> SEQ ID NO 14
<211> LENGTH: 58
<212> TYPE: DNA
<213> ORGANISM: Artificial Sequence
<220> FEATURE:
<223> OTHER INFORMATION: primer

<400> SEQUENCE: 14
gagctttcaa acattgcaac aaagatggat aagaagaacc agaagattta gtattacc      58

<210> SEQ ID NO 15
<211> LENGTH: 60
<212> TYPE: DNA
<213> ORGANISM: Artificial Sequence

```
<220> FEATURE:
<223> OTHER INFORMATION: primer

<400> SEQUENCE: 15
gttgcaatgt tgaaagctc cagttttgtc tgattcttct tgtaaatctt cttacccagg      60

<210> SEQ ID NO 16
<211> LENGTH: 59
<212> TYPE: DNA
<213> ORGANISM: Artificial Sequence
<220> FEATURE:
<223> OTHER INFORMATION: primer

<400> SEQUENCE: 16
ccaaaaaacc aacacaaatc atattaccag taatttgacc tgggtaagaa gatttacaa      59

<210> SEQ ID NO 17
<211> LENGTH: 60
<212> TYPE: DNA
<213> ORGANISM: Artificial Sequence
<220> FEATURE:
<223> OTHER INFORMATION: primer

<400> SEQUENCE: 17
gatttgtgtt ggttttttgg aaggtggtaa agattcttgt caaggtgatt ctggtggtcc      60

<210> SEQ ID NO 18
<211> LENGTH: 57
<212> TYPE: DNA
<213> ORGANISM: Artificial Sequence
<220> FEATURE:
<223> OTHER INFORMATION: primer

<400> SEQUENCE: 18
ccaagaaaca ataccttgca attgaccatt acaaacaact ggaccaccag aatcacc        57

<210> SEQ ID NO 19
<211> LENGTH: 51
<212> TYPE: DNA
<213> ORGANISM: Artificial Sequence
<220> FEATURE:
<223> OTHER INFORMATION: primer

<400> SEQUENCE: 19
gcaaggtatt gtttcttggg gttatggttg tgctcaaaaa aataaaccag g              51

<210> SEQ ID NO 20
<211> LENGTH: 90
<212> TYPE: DNA
<213> ORGANISM: Artificial Sequence
<220> FEATURE:
<223> OTHER INFORMATION: primer

<400> SEQUENCE: 20
gcgtctagac taattagcag caatagtttg ttgaatccaa ttaacataat tacaaacttt     60
agtgtaaaca cctggtttat ttttttgagc                                     90

<210> SEQ ID NO 21
<211> LENGTH: 48
<212> TYPE: DNA
<213> ORGANISM: Artificial Sequence
<220> FEATURE:
<223> OTHER INFORMATION: primer

<400> SEQUENCE: 21
```

```
ccgggaattc gatgatgatg ataaaattgt tggtggttat acttgtgc                48
```

<210> SEQ ID NO 22
<211> LENGTH: 687
<212> TYPE: DNA
<213> ORGANISM: Artificial Sequence
<220> FEATURE:
<223> OTHER INFORMATION: Synthetic gene

<400> SEQUENCE: 22

```
gatgatgatg ataaaattgt tggtggttat acttgtgctg ctaattctat tccatatcaa     60
gtttctttaa attctggttc tcattttgt ggtggttctt tgattaattc tcaatgggtt    120
gtttctgctg ctcattgtta caaatcaaga atccaagtta gattgggtga acataatatt    180
gatgttttgg aaggtaatga acaatttatt aatgctgcta aaattattac tcatccaaat    240
tttaatggta atactttgga taatgatatt atgttgatta aattgtcttc tccagctact    300
ttaaattcaa gagttgctac tgtttctttg ccaagatctt gtgctgctgc tggtactgaa    360
tgtttgattt ctggttgggg taatactaaa tcttctggtt cttcttatcc atctttgttg    420
caatgtttga agctccagt tttgtctgat tcttcttgta atcttctta cccaggtcaa     480
attactggta atatgatttg tgttggtttt ttggaaggtg gtaaagattc ttgtcaaggt    540
gattctggtg gtccagttgt ttgtaatggt caattgcaag gtattgtttc ttggggttat    600
ggttgtgctc aaaaaaataa accaggtgtt tacactaaag tttgtaatta tgttaattgg    660
attcaacaaa ctattgctgc taattag                                        687
```

<210> SEQ ID NO 23
<211> LENGTH: 228
<212> TYPE: PRT
<213> ORGANISM: Artificial Sequence
<220> FEATURE:
<223> OTHER INFORMATION: Shortened Trypsinogen

<400> SEQUENCE: 23

```
Asp Asp Asp Asp Lys Ile Val Gly Gly Tyr Thr Cys Ala Ala Asn Ser
1               5                   10                  15

Ile Pro Tyr Gln Val Ser Leu Asn Ser Gly Ser His Phe Cys Gly Gly
            20                  25                  30

Ser Leu Ile Asn Ser Gln Trp Val Val Ser Ala Ala His Cys Tyr Lys
        35                  40                  45

Ser Arg Ile Gln Val Arg Leu Gly Glu His Asn Ile Asp Val Leu Glu
    50                  55                  60

Gly Asn Glu Gln Phe Ile Asn Ala Ala Lys Ile Ile Thr His Pro Asn
65                  70                  75                  80

Phe Asn Gly Asn Thr Leu Asp Asn Asp Ile Met Leu Ile Lys Leu Ser
                85                  90                  95

Ser Pro Ala Thr Leu Asn Ser Arg Val Ala Thr Val Ser Leu Pro Arg
            100                 105                 110

Ser Cys Ala Ala Ala Gly Thr Glu Cys Leu Ile Ser Gly Trp Gly Asn
        115                 120                 125

Thr Lys Ser Ser Gly Ser Ser Tyr Pro Ser Leu Leu Gln Cys Leu Lys
    130                 135                 140

Ala Pro Val Leu Ser Asp Ser Ser Cys Lys Ser Ser Tyr Pro Gly Gln
145                 150                 155                 160

Ile Thr Gly Asn Met Ile Cys Val Gly Phe Leu Glu Gly Gly Lys Asp
                165                 170                 175
```

```
Ser Cys Gln Gly Asp Ser Gly Gly Pro Val Val Cys Asn Gly Gln Leu
            180                 185                 190

Gln Gly Ile Val Ser Trp Gly Tyr Gly Cys Ala Gln Lys Asn Lys Pro
        195                 200                 205

Gly Val Tyr Thr Lys Val Cys Asn Tyr Val Asn Trp Ile Gln Gln Thr
    210                 215                 220

Ile Ala Ala Asn
225

<210> SEQ ID NO 24
<211> LENGTH: 5
<212> TYPE: PRT
<213> ORGANISM: Artificial Sequence
<220> FEATURE:
<223> OTHER INFORMATION: Enteropeptidase recognition sequence

<400> SEQUENCE: 24

Asp Asp Asp Asp Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Enteropeptidase recognition sequence plus
      additional amino acid

<400> SEQUENCE: 25

Asp Asp Asp Asp Lys Ile
1               5

<210> SEQ ID NO 26
<211> LENGTH: 7
<212> TYPE: PRT
<213> ORGANISM: Artificial Sequence
<220> FEATURE:
<223> OTHER INFORMATION: Enteropeptidase recognition sequence

<400> SEQUENCE: 26

Glu Phe Asp Asp Asp Asp Lys
1               5

<210> SEQ ID NO 27
<211> LENGTH: 230
<212> TYPE: PRT
<213> ORGANISM: Artificial Sequence
<220> FEATURE:
<223> OTHER INFORMATION: Shortened Trypsinogen

<400> SEQUENCE: 27

Glu Phe Asp Asp Asp Asp Lys Ile Val Gly Gly Tyr Thr Cys Ala Ala
1               5                   10                  15

Asn Ser Ile Pro Tyr Gln Val Ser Leu Asn Ser Gly Ser His Phe Cys
            20                  25                  30

Gly Gly Ser Leu Ile Asn Ser Gln Trp Val Val Ser Ala Ala His Cys
        35                  40                  45

Tyr Lys Ser Arg Ile Gln Val Arg Leu Gly Glu His Asn Ile Asp Val
    50                  55                  60

Leu Glu Gly Asn Glu Gln Phe Ile Asn Ala Ala Lys Ile Ile Thr His
65                  70                  75                  80

Pro Asn Phe Asn Gly Asn Thr Leu Asp Asn Asp Ile Met Leu Ile Lys
                85                  90                  95
```

```
Leu Ser Ser Pro Ala Thr Leu Asn Ser Arg Val Ala Thr Val Ser Leu
            100             105             110

Pro Arg Ser Cys Ala Ala Ala Gly Thr Glu Cys Leu Ile Ser Gly Trp
        115             120             125

Gly Asn Thr Lys Ser Ser Gly Ser Ser Tyr Pro Ser Leu Leu Gln Cys
        130             135             140

Leu Lys Ala Pro Val Leu Ser Asp Ser Ser Cys Lys Ser Ser Tyr Pro
145                 150             155                 160

Gly Gln Ile Thr Gly Asn Met Ile Cys Val Gly Phe Leu Glu Gly Gly
                165             170             175

Lys Asp Ser Cys Gln Gly Asp Ser Gly Gly Pro Val Val Cys Asn Gly
            180             185             190

Gln Leu Gln Gly Ile Val Ser Trp Gly Tyr Gly Cys Ala Gln Lys Asn
        195             200             205

Lys Pro Gly Val Tyr Thr Lys Val Cys Asn Tyr Val Asn Trp Ile Gln
    210             215             220

Gln Thr Ile Ala Ala Asn
225             230
```